(12) United States Patent
Roychowdhury

(10) Patent No.: US 7,763,049 B2
(45) Date of Patent: Jul. 27, 2010

(54) ORTHOPEDIC FIXATION CONNECTOR

(75) Inventor: Suranjan Roychowdhury, Plymouth, MN (US)

(73) Assignee: Zimmer Spine, Inc., Minneapolis, MN (US)

( * ) Notice: Subject to any disclaimer, the term of this patent is extended or adjusted under 35 U.S.C. 154(b) by 448 days.

(21) Appl. No.: 10/865,169

(22) Filed: Jun. 9, 2004

(65) Prior Publication Data
US 2005/0277924 A1    Dec. 15, 2005

(51) Int. Cl.
*A61B 17/70* (2006.01)
(52) U.S. Cl. ...................................... 606/246
(58) Field of Classification Search .................. 606/60, 606/61, 72, 73, 246, 264, 265, 267, 273–279, 606/300, 301, 305–308, 319
See application file for complete search history.

(56) References Cited

U.S. PATENT DOCUMENTS

| | | | |
|---|---|---|---|
| 255,428 A | 3/1882 | Graham |
| 590,294 A | 9/1897 | Archer |
| 3,618,135 A | 11/1971 | Weller |
| 4,378,187 A | 3/1983 | Fullerton |
| 4,419,026 A | 12/1983 | Leto |
| 4,653,969 A | 3/1987 | Summerlin et al. |
| 4,684,284 A | 8/1987 | Bradley, Jr. |
| 4,737,059 A | 4/1988 | Batten |
| 4,822,223 A | 4/1989 | Williams |
| 4,836,196 A | 6/1989 | Park et al. |
| 4,854,304 A | 8/1989 | Zielke |
| 4,887,595 A | 12/1989 | Heinig et al. |
| 4,887,596 A | 12/1989 | Sherman |
| 4,946,458 A | 8/1990 | Harms et al. |
| 4,950,269 A | 8/1990 | Gaines, Jr. |
| 5,002,542 A | 3/1991 | Frigg |
| 5,129,900 A | 7/1992 | Asher et al. |
| 5,133,717 A | 7/1992 | Chopin |
| 5,261,913 A | 11/1993 | Marnay |
| 5,312,405 A | 5/1994 | Korotko et al. |
| 5,324,150 A | 6/1994 | Fullerton |
| 5,377,395 A | 1/1995 | Maier et al. |
| 5,427,488 A | 6/1995 | Fullerton et al. |

(Continued)

FOREIGN PATENT DOCUMENTS

DE    197 20 782 A1    11/1998

(Continued)

OTHER PUBLICATIONS

Centerpulse Spine-Tech Optima™ Spinal Fixation System Surgical Technique, pp. 3-18, 2003.

(Continued)

*Primary Examiner*—Eduardo C. Robert
*Assistant Examiner*—David Comstock
(74) *Attorney, Agent, or Firm*—Crompton, Seager & Tufte, LLC.

(57) ABSTRACT

An orthopedic fixation connector and system is provided. The orthopedic fixation system includes bone anchors and linking elements that are coupled together to form a stabilization construct. The linking elements are fixed relative to the bone anchors by clamping arrangements. The clamping arrangements include first linear interlock components coupled to the anchors and second linear interlock components that linearly interlock with the first interlock components to clamp the linking elements at desired positions relative to the anchors.

17 Claims, 15 Drawing Sheets

U.S. PATENT DOCUMENTS

| | | | |
|---|---|---|---|
| 5,487,744 A | 1/1996 | Howland | |
| 5,520,689 A * | 5/1996 | Schlapfer et al. | 606/61 |
| 5,545,165 A | 8/1996 | Biedermann et al. | |
| 5,549,608 A | 8/1996 | Errico et al. | |
| 5,569,247 A | 10/1996 | Morrison | |
| 5,591,166 A | 1/1997 | Bernhardt et al. | |
| 5,613,816 A | 3/1997 | Cabahug | |
| 5,628,740 A | 5/1997 | Mullane | |
| 5,653,765 A | 8/1997 | McTighe et al. | |
| 5,667,508 A * | 9/1997 | Errico et al. | 606/73 |
| 5,683,390 A | 11/1997 | Metz-Stavenhagen et al. | |
| 5,692,865 A | 12/1997 | Pratt | |
| 5,716,357 A | 2/1998 | Rogozinski | |
| 5,725,527 A | 3/1998 | Biedermann et al. | |
| 5,733,286 A * | 3/1998 | Errico et al. | 606/61 |
| 5,749,690 A | 5/1998 | Kutz | |
| 5,788,443 A | 8/1998 | Cabahug | |
| 5,800,108 A | 9/1998 | Cabahug | |
| 5,800,435 A | 9/1998 | Errico et al. | |
| 5,816,761 A | 10/1998 | Cassatt et al. | |
| 5,879,350 A | 3/1999 | Sherman et al. | |
| 5,931,840 A | 8/1999 | Goble et al. | |
| 6,050,997 A | 4/2000 | Mullane | |
| 6,063,090 A | 5/2000 | Schlapfer | |
| 6,074,391 A * | 6/2000 | Metz-Stavenhagen et al. | 606/61 |
| 6,077,262 A * | 6/2000 | Schlapfer et al. | 606/61 |
| 6,090,111 A | 7/2000 | Nichols | |
| 6,102,952 A | 8/2000 | Koshino | |
| 6,162,234 A | 12/2000 | Freedland et al. | |
| 6,224,598 B1 * | 5/2001 | Jackson | 606/61 |
| RE37,227 E | 6/2001 | Brodbeck | |
| 6,254,602 B1 | 7/2001 | Justis | |
| 6,296,642 B1 * | 10/2001 | Morrison et al. | 606/61 |
| 6,302,888 B1 * | 10/2001 | Mellinger et al. | 606/73 |
| 6,355,040 B1 * | 3/2002 | Richelsoph et al. | 606/61 |
| 6,371,957 B1 | 4/2002 | Amrein et al. | |
| 6,440,132 B1 | 8/2002 | Jackson | |
| 6,565,565 B1 * | 5/2003 | Yuan et al. | 606/61 |
| 6,602,255 B1 | 8/2003 | Campbell et al. | |
| 6,613,050 B1 | 9/2003 | Wagner et al. | |
| 6,623,485 B2 | 9/2003 | Doubler et al. | |
| 6,652,526 B1 * | 11/2003 | Arafiles | 606/61 |
| 6,712,544 B2 | 3/2004 | Kruger et al. | |
| 6,726,689 B2 * | 4/2004 | Jackson | 606/73 |
| 6,884,244 B1 * | 4/2005 | Jackson | 606/73 |
| 6,896,677 B1 * | 5/2005 | Lin | 606/61 |
| 2002/0114680 A1 | 8/2002 | Stoewer et al. | |
| 2003/0073996 A1 | 4/2003 | Doubler et al. | |
| 2003/0149487 A1 | 8/2003 | Doubler et al. | |
| 2004/0006342 A1 | 1/2004 | Altarac et al. | |
| 2004/0181224 A1 * | 9/2004 | Biedermann et al. | 606/61 |
| 2004/0260283 A1 * | 12/2004 | Wu et al. | 606/61 |

FOREIGN PATENT DOCUMENTS

| | | |
|---|---|---|
| DE | 100 05 386 A1 | 8/2001 |
| EP | 1 354 563 | 10/2003 |
| WO | 0015125 A1 | 3/2000 |
| WO | WO 03/043511 | 5/2003 |
| WO | WO 2004/064653 | 8/2004 |

OTHER PUBLICATIONS

Centerpulse Spine-Tech Optima™ Spinal Fixation System Product Information, 2 pgs., 2003.

Centerpulse Spine-Tech ST360'™ Spinal Fixation System Product Information, 3 pgs., 2003.

Sulzer Spine-Tech Surgical Technique for Posterior Lumbar Fixation, 21 pgs., 2001.

Sulzer Spine-Tech Silhouette Spinal Fixation System: System Overview, 4 pgs., 1999.

* cited by examiner

ORTHOPEDIC FIXATION CONNECTOR

TECHNICAL FIELD

The principles disclosed herein relate generally to bone fixation and stabilization systems. More specifically, the disclosure relates to intervertebral connection systems suited for stabilization of the spine.

BACKGROUND

Chronic back problems cause pain and disability for a large segment of the population. In many cases, the chronic back problems are caused by intervertebral disc disease and deterioration and loss of stability of the intervertebral joint. Examples of these spinal conditions include degenerative disc disease, scoliosis, spondylolithesis, spinal stenosis, etc. Stabilization and/or arthrodesis of the intervertebral joint can reduce the pain associated with movement of a diseased or deteriorated intervertebral joint. In order to allow for development of a solid intervertebral fusion, the spine has to be stabilized.

Spinal stabilization systems have been developed to stabilize the vertebrae to allow for fusion or stabilization of diseased intervertebral joints. One type of spinal stabilization system includes connectors and rods that are used to stabilize the spine. Some examples of such spinal stabilization systems are disclosed in U.S. Pat. Nos. 6,613,050 B1; 6,371,957 B1; 6,050,997; 5,879,350; 5,725,527; 5,628,740; 5,545,165, the entire disclosures of which are incorporated herein by reference. In these systems, connectors are anchored to the vertebral bodies desired to be stabilized by anchoring structures such as screws or hooks. One or more connecting rods are then secured to the connectors to form a connector/rod construct that stabilizes the vertebral bodies to which the connectors are secured.

In many known stabilization systems, threaded nuts are used to secure the rods to the connectors. Typically, a torque wrench or similar device is used to achieve the required torques to finally secure the connector/rod construct. To prevent torque from being transferred to the patient while tightening the nut, an anti-torque device is frequently used in combination with the torque wrench. The effective use of the torque wrench and anti-torque device can be difficult and often is dependent upon the strength and experience of the surgeon. What are needed are alternative spine stabilization fastening techniques that do not require the use of torque.

SUMMARY

One aspect of the present disclosure relates to spine fixation systems and other orthopedic fixation systems utilizing non-threaded, linearly-locking mechanisms for securing components together. The use of linear-locking mechanisms allows for the fixation of a first component to a second component in an orthopedic construct without the difficulties of using torque for tightening purposes.

Another aspect of the disclosure relates to orthopedic stabilization systems that use ratcheting-type securement arrangements for fixing together the various components of a stabilization construct. The use of linear ratcheting type securement arrangements ensures progressively closer juxtaposition of the components, allows for an optimum level of fixation, and facilitates revising the securement arrangement when required, without the difficulties that are associated with the use of torque systems.

It should be noted that, at various locations throughout the specification, guidance is provided through lists of examples. The examples are for illustrative purposes and are not intended to limit the scope of the invention.

DETAILED DESCRIPTION

One aspect of the present disclosure relates to a clamping arrangement for use with an orthopedic or bone fixation system. Preferably, the clamping arrangement is adapted to generate a clamping force for clamping a component at a desired position without requiring the use of torque. The clamping arrangement preferably includes first and second linear interlock components adapted to interlock with one another when the components are linearly inserted together. Preferably, at least one of the interlock components is configured to elastically deform (i.e., deform generally within the elastic limit of the component) when the components are inserted together. As the linear insertion process continues, the elastically deformed component self-returns (e.g., snaps back) towards a non-deformed position in which the components are interlocked together. When the first and second linear interlock components are interlocked, the components are preferably adapted to apply a clamping force to a third component (e.g., a rod) such that the third component is locked/fixed in place relative to the interlock components.

Although the disclosure will be described in terms of a spinal fixation system, the fixation system can be utilized in any type of orthopedic fixation.

In one embodiment, the fixation system includes anchors adapted to be secured to bones such as vertebral bodies. The fixation system also includes linking elements (e.g. rods, plates or other members) for linking the anchors together. The fixation system also includes a clamping arrangement for fixing the linking elements to the anchors such that the linking elements are not free to slide relative to the anchors. In certain embodiments, the clamping arrangement includes first linear interlock components coupled to the anchors and second linear interlock components adapted to linearly interlock with the first linear interlock components to clamp or otherwise fix the linking elements relative to the anchors. The first and second interlock components preferably allow the linking elements to be clamped in position without requiring torque. In certain embodiments, the first linear interlock components include structures such as receivers (e.g. saddles). In certain embodiments, the second linear interlock components include retainers such as plugs, caps, rings or other structures.

The invention will now be described by reference to the several drawing figures. The functional features of the invention can be embodied in any of a number of specific configurations. It will be appreciated, however, that the illustrated embodiments are provided for descriptive purposes and should not be used to limit the invention.

Figure 1:
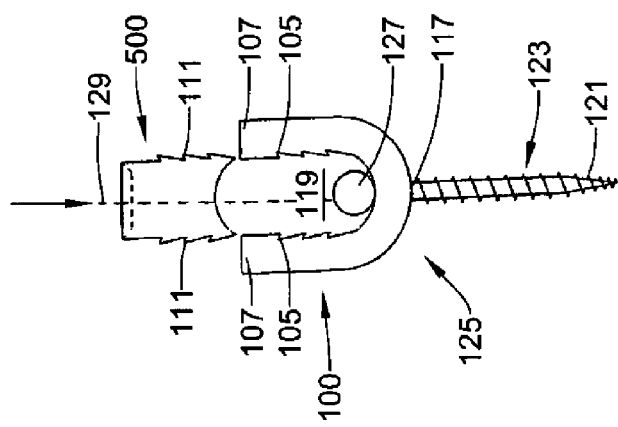
FIG. 1 is a side view of one embodiment of a spinal fixation connector having features that are examples of inventive aspects disclosed herein.

FIG. 1 illustrates one embodiment of a spinal fixation connector 125 used in stabilization of the vertebrae. The fixation connector 125 includes a bone engagement structure 123 (i.e., an anchor) adapted for securing the connector 125 to a bone such as a vertebral body. The connector 125 also includes a first linear interlock component in the form of a receiver 100 coupled to the bone engagement structure 123. The receiver 100 defines an interior pocket 119 or receptacle for receiving a linking element 127 such as a rod or other member. The connector 125 further includes a second linear interlock component in the form of a retaining member (e.g., a plug 500) adapted to be inserted into the pocket 119 to clamp or otherwise secure the linking element 127 within the pocket 119. The plug 500 is adapted to be linearly inserted into the pocket 119 along insertion line 129. The receiver 100 and the plug 500 include intermating interlock structures 105, 111 that interlock to fix the retaining member 500 at a desired insertion depth within the pocket 119. The interlock structures 105, 111 preferably hold the plug 500 at a depth where the linking element 127 is clamped between the plug 500 and the receiver 100.

Figure 2:
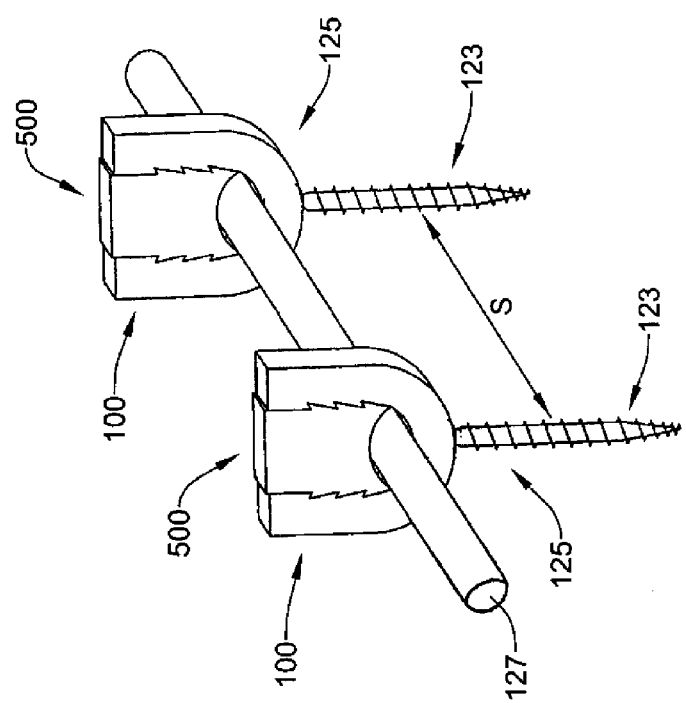
FIG. 2 is a perspective view of a stabilization construct including fixation connectors of the type shown in FIG. 1.
Figure 3:
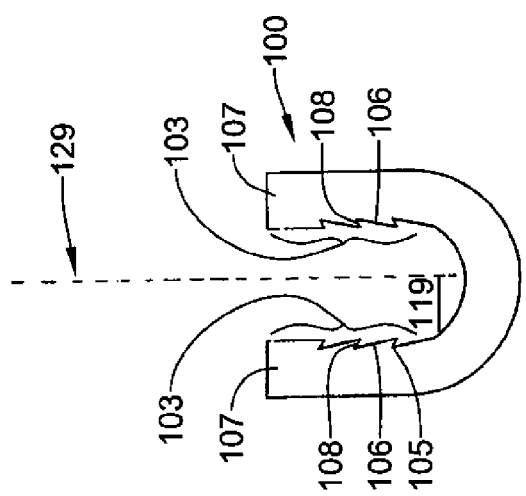
FIG. 3 is a side view of a saddle of the fixation connector of FIG. 1.
Figure 4:
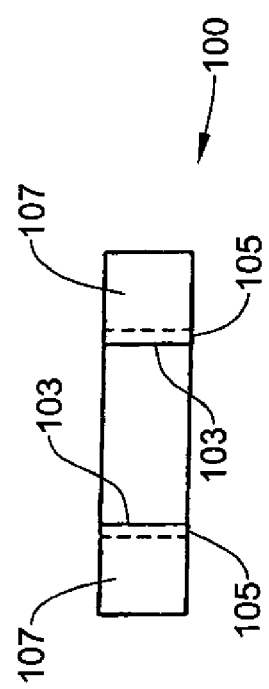
FIG. 4 is a top view of the saddle of FIG. 3.

In general use, two of the connectors 125 are secured to adjacent vertebral bodies desired to be stabilized. The vertebral bodies are then distracted or compressed to a desired spacing. Once desired position is achieved, linking element 127 is laid within the pockets 119 of the connectors 125 so as to extend between the distracted or compressed vertebral bodies across the spacing between the vertebral bodies. The plugs 500 are then inserted into the pockets 119 to clamp the linking element 127 within the pockets 119 as shown in FIG. 2. The plugs 500 preferably clamp the linking element 127 with sufficient force to prevent the linking element 127 from sliding relative to the connectors 125. In this manner, the linking element 127 functions as a brace or stabilizer for maintaining the desired spacing S between the vertebral bodies.

As shown in FIGS. 1-4, the receiver 100 of the fixation connector 125 is depicted as a U-shaped saddle. The saddle includes two legs 107 between which the pocket 119 is defined. The legs 107 include opposing interior surfaces 103. The interior surfaces 103 also include opposing ramp surfaces 106. The ramp surfaces 106 are preferably oriented at oblique angles relative to the line of insertion 129. The interior surfaces 103 also include oppositely positioned locking surfaces 108. The locking surfaces 108 are oriented at an angle closer to 90° relative to the line of insertion as compared to the ramp surfaces 106. The intersection of the locking surfaces 108 with the ramp surfaces 106 define discrete locking structures 105 (e.g., ratchet teeth) within the pocket of the receiver 100. The ramp surfaces 106 generally define a depth between each discrete locking structure 105 and also guide the plug 500 along the interior surface of the pocket 119 from one discrete locking structure 105 to the next.

Figure 5:
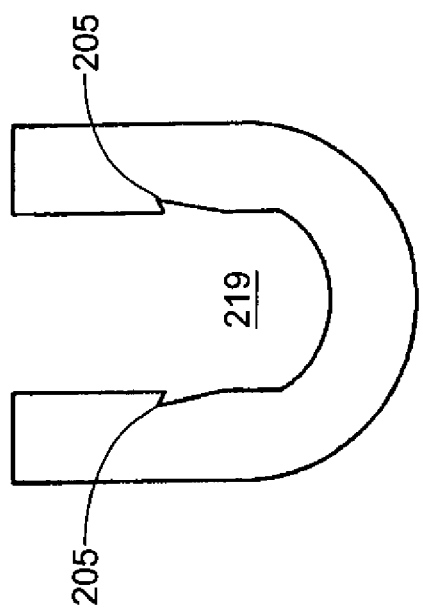
FIG. 5 is a side view of an alternative saddle having features that are examples of inventive aspects disclosed herein.

FIG. 5 illustrates another embodiment of a receiver 200 of the fixation connector. In this embodiment, the receiver 200 is depicted as a U-shaped saddle including only one set of discrete locking structures 205 (e.g. locking teeth) within the pocket 219 of the saddle. It will be appreciated that the embodiment illustrated in FIG. 5 is only a representative example and that the receiver of the fixation connector can include any number of discrete locking positions.

As shown in FIGS. 1 and 2, the bone engaging structure 123 is depicted as a bone screw having threads. In other embodiments, other types of anchors such as hooks, pins, expandable anchors, barbed anchors or other structures adapted for securing to bone can also be used. The bone screw 123 includes a top end 117 and a bone-engaging end 121. In the embodiment shown in FIGS. 1 and 2, the bone screw 123 is depicted as being integral with the receiver 100. As will be discussed further below, other embodiments of the spinal fixation connector can include bone engagement structures that are non-integrally coupled to the receiver to allow for polyaxial adjustment of the position of the bone engagement structure relative to that of the receiver.

Figure 6:
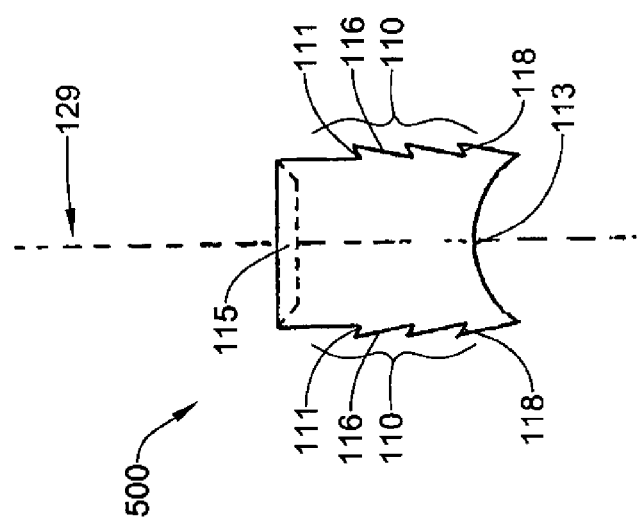
FIG. 6 is a side view of a locking plug of the fixation connector of FIG. 1.

As shown in FIG. 6, the plug includes a bottom end 113 adapted to clamp down the linking element 127 within the pocket 119 of the receiver 100 and prevent the linking element 127 from sliding relative to the connector 125. The plug 500 also includes a top end 115. The top end 115 of the plug is not limited to any specific shape and can be configured according to a desired functionality. The plug also includes outer sidewalls 110. The outer sidewalls 110 include ramp surfaces 116. The ramp surfaces 116 are preferably oriented at oblique angles relative to the line of insertion 129. The outer sidewalls also include locking surfaces 118. The locking surfaces 118 are oriented at angles closer to 90° relative to the line of insertion 129 than the ramp surfaces 116. The intersection of the locking surfaces 118 with the ramp surfaces 116 define discrete locking structures 111 (e.g., ratchet teeth) on the outer sidewalls 110 of the plug 500. The ramp surfaces 116 generally define a depth between each discrete locking structure 111 and also guide the plug 500 along the interior surface of the pocket 119 from one discrete locking structure 111 to the next.

Figure 7:
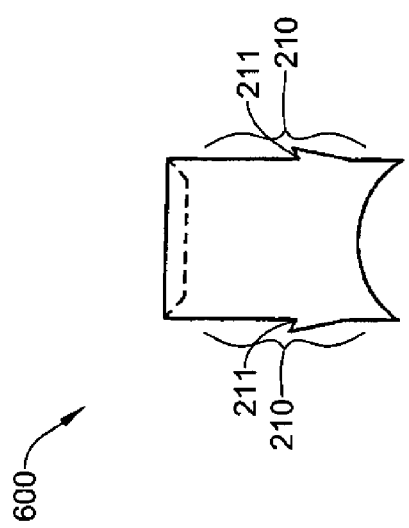
FIG. 7 is a side view of a locking plug adapted for use with the saddle of FIG. 5.

FIG. 7 illustrates a plug 600 adapted for use with the receiver 200 of FIG. 5. The plug 600 is substantially identical to the embodiment shown in FIG. 6, except that the plug 600 includes only one set of discrete locking structures 211 on the outer sidewalls 210 of the plug 600. It will be appreciated that the embodiment illustrated in FIG. 7 is only a representative example and that any number of discrete locking structures (e.g., teeth) can be used.

Figure 8:
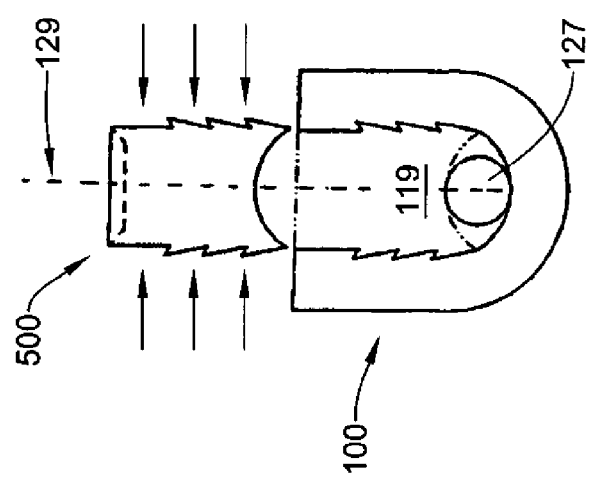
FIG. 8 illustrates another spinal fixation connector having features that are examples of inventive aspects disclosed herein, the connector includes a compressible plug.

FIG. 8 is an illustrative example of how the plug 500 can interlock with the receiver 100 and clamp the linking element 127. The plug 500 may have a snap-fit connection with the receiver 100. As used herein, the phrase "snap-fit connection" means a connection provided by a resilient structure (e.g., a tooth) that flexes or deforms past a retaining structure and moves to a locking or retaining position by the inherent elasticity of the resilient structure. In the embodiment shown in FIG. 8, the retaining member is depicted as a plug 500 having teeth adapted to elastically deform when the plug is linearly inserted within the receiver 100 of the spinal fixation connector 125. The ability of the plug 500 to elastically deform can be provided by the mechanical properties of the material of the plug 500 and/or a combination of structures to enhance deformability and the mechanical properties of the material. The plug 500 and the receiver 100 can be manufactured from materials of various rigidity such as: Titanium, Nitinol, Stainless Steel, Thermoplastic polymers or Thermoset polymers.

In use, the plug 500 is linearly inserted into the receiver 100 along the line of insertion 129. When the plug is pressed into the pocket of the receiver 100, the ramp surfaces 106 of the receiver 100 make contact with the ramp surfaces 116 of the plug 500 causing the locking structures 111 to deflect inwardly from a non-deformed orientation to an elastically deformed orientation. The inward deformation occurs until the locking surfaces 108 of the receiver 100 pass the corresponding locking surfaces 118 of the plug 500. At this point, the locking structures 111 of the plug 500 snap outwardly towards the non-deformed orientation causing the discrete locking structures 111 (e.g., ratchet teeth) of the plug 500 to interlock the locking structures (e.g., ratchet teeth) 105 of the receiver 100. As the plug 500 is forced deeper into the pocket 119 of the receiver 100, the ramp surfaces 106, 116 again cooperate to deflect the locking structures 111 of the plug 500 inwardly until the locking structures 111 interlock with the next set of locking structures 105 of the receiver 100. This deformation process is repeated until the plug 500 is locked into position at the desired depth within the pocket 119 of the receiver 100 to securely clamp the linking element 127.

Figure 9:
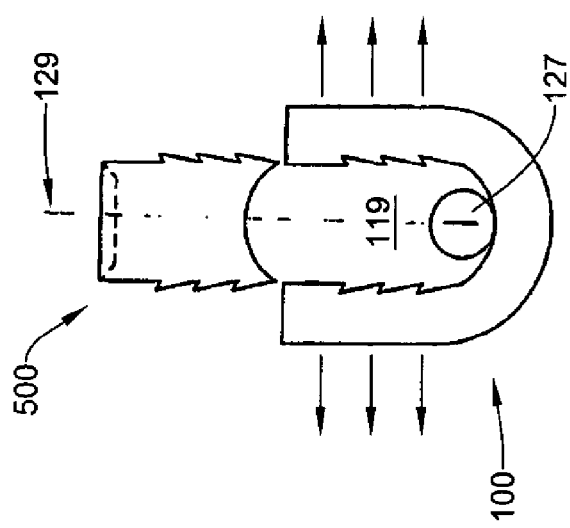
FIG. 9 illustrates a further spinal fixation connector having features that are examples of inventive aspects disclosed herein, the connector includes an expandable saddle.

In the embodiment FIG. 9, the locking structures 105 of the receiver 100 deflect outwardly when the plug 500 is pressed downwardly into the pocket 119. For example, as the plug 500 is pressed into the pocket 119, the ramp surfaces 106, 116 engage one another causing the locking structures 105 to deflect outwardly to permit clearance of the locking structures 111. Once the locking structures 111 move downwardly past their corresponding locking structures 105 on the receiver 100, the locking structures 105 resiliently snap inwardly to an interlocked orientation. This process is repeated at progressively deeper interlock positions until the plug 500 reaches a position where the rod 127 is securely clamped within the receiver 100.

It will be appreciated that elastic deformation suitable for providing a snap-fit connection between the plug and the receiver 100 can be provided by deflection of the locking structures 111, deflection of the locking structures 105, flexing of the legs 107, compression of the body of the plug 500, or any combination thereof.

Figure 10:
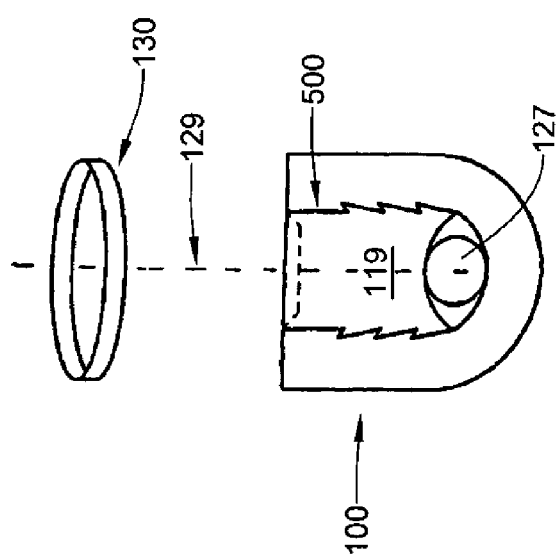
FIG. 10 illustrates another the spinal fixation connector having features that are examples of inventive aspects disclosed herein, the connector includes an anti-slide retention ring.

Once the plug 500 is snapped into the desired position within the receiver 100 and the linking element 127 is fixed in position, an anti-slide device 130 depicted as a band 130 in FIG. 10 can be used to prevent lateral sliding of the plug 500 within the pocket 119 of the receiver 100. In other embodiments, other types of anti-slide devices such as tapes, clamps, fasteners or other structures can be used. The band 130 can be placed around the legs 107 of the receiver 100 to securely station the plug 500 within the receiver 100. The band 130 opposes any sliding motion of the plug 500 in the direction perpendicular to the line of insertion 129. Since the discrete interlocking structures 105 of the receiver and the interlocking structures 111 of the plug 500 prevent the movement of the plug 500 in the direction of the insertion line 129, the plug is thus securely fixed within the receiver 100. If is becomes necessary to remove the plug 500 (e.g., for corrective surgery) the anti-slide band 130 can be removed and the plug 500 can be laterally slid from the receiver 100. Alternatively, a tool adapted to spread the legs 107 of the receiver 100 outwardly can be used to facilitate removal of the plug 500 from the receiver 100.

Figure 11:
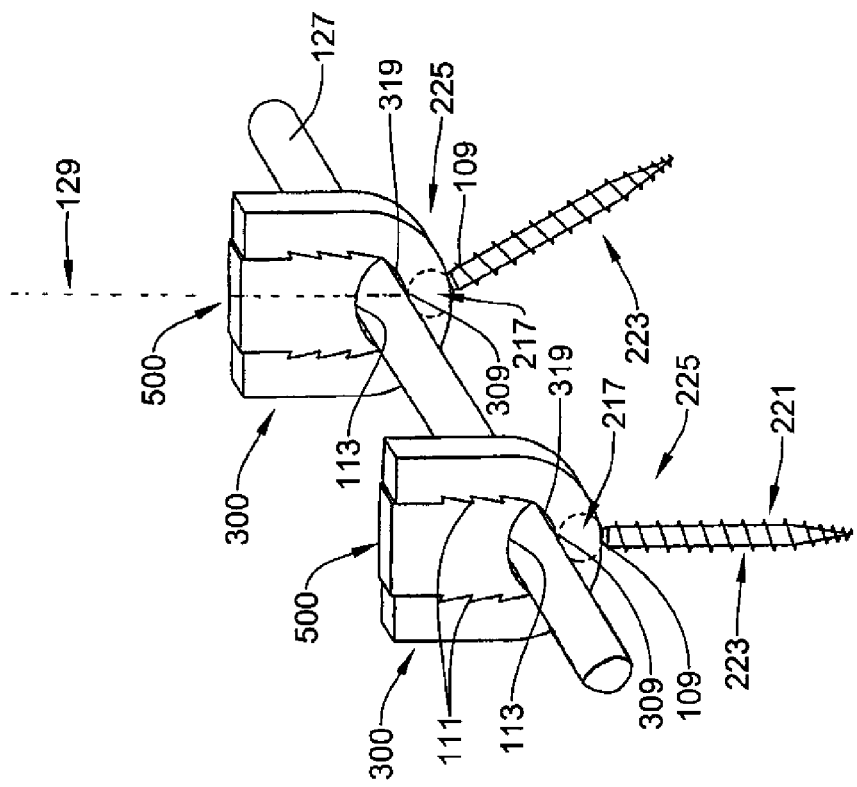
FIG. 11 illustrates a stabilization construct having features that are examples of inventive aspects disclosed herein, the construct includes connectors including poly-axial anchors.

FIG. 11 illustrates another embodiment of a fixation connector 225 used in stabilization of the vertebrae. The fixation connector of FIG. 11 is similar to the fixation connector illustrated in FIGS. 1 and 2, except the connector 225 includes a receiver 300 that is not integral with a corresponding bone screw 223. In the embodiment shown in FIG. 11, the bone screw 223 is movably coupled to the receiver 300 to allow the axial position of the bone screw 223 to be angularly adjusted relative to the receiver 300. The receiver 300 defines an interior pocket 319 or receptacle for receiving a linking element 127 such as a rod or other member. Similar to the embodiment of FIG. 2, a plug 500 can be linearly inserted into the pocket to securely clamp the linking element 127 within the receiver 300.

The bone screw 223 of FIG. 11 includes a spherically shaped top end 217 and a threaded end 221. The threaded end 221 of the screw 223 is sized to fit through a bottom through hole 109 of the receiver 300. The spherical top end 217 is adapted to seat within a corresponding spherical cavity 309 within the receiver 300. In this embodiment, the top end 217 is adapted to allow the bone screw 223 a range of angular motion throughout a 360-degree pattern relative to the insertion line 129. The top end 217 of the anchor 223 is sized to fit inside the spherically shaped cavity 309 such that the top end 217 of the anchor 223 is free to pivot within the cavity 309 allowing for angular adjustment of the bone screw 223 relative to the receiver 300.

In general use, two of the connectors 225 are secured to adjacent vertebral bodies desired to be stabilized. The vertebral bodies are then distracted or compressed to a desired spacing. Once desired position is achieved, linking element 127 is laid within the pockets 319 of the receivers 300. Adjusting the angular position of the receivers 300 relative to the bone screws 223 facilitates insertion of the linking element 127 into the receivers 300. The plugs 500 are then inserted into the pockets 319 to clamp the linking element 127 within the pockets 319 and to clamp the bone screws 223 at the desired angle relative to the receivers 300. The plugs 500 preferably clamp the linking element 127 with sufficient force to prevent the linking element 127 from sliding relative to the connector 225. The linking element 127 is forced against the top end 217 of the bone screw 223 causing the spherical underside of the top end 217 to be clamped into the spherical cavity 309 of the receiver 300 to prevent pivotal movement of the bone screws 223 relative to the receivers 300.

Figure 12:
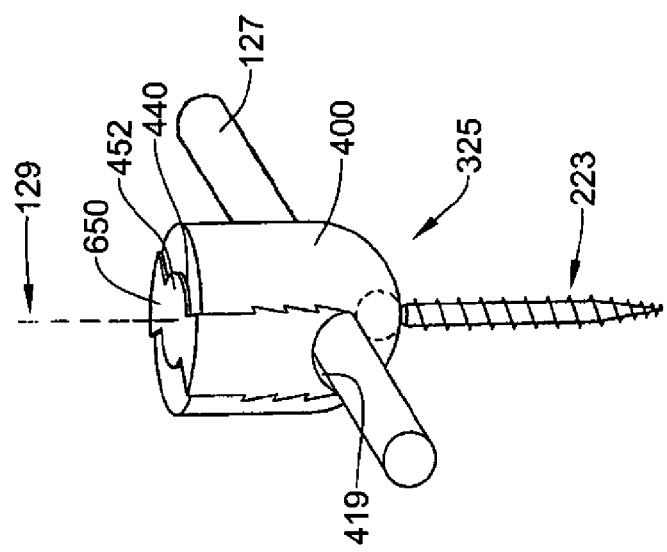
FIG. 12 is a perspective view of a further spinal fixation connector having features that are examples of inventive aspects disclosed herein, the fixation connector includes an anti-slide plug.

FIG. 12 illustrates another embodiment of a fixation connector 325 used in the stabilization of the vertebrae. The fixation connector 325 of FIG. 12 is similar to the embodiment shown in FIG. 11, except the connector 325 includes a receiver member 400 adapted for preventing lateral sliding of a plug 650 in a direction perpendicular to the insertion line 129. The receiver 400 includes a pocket 419 shaped to receive the plug 650 in the direction of the insertion line 129. Once interlocked inside the pocket 419, the plug 650 is fixed in a locked position. The embodiment of the fixation connector 325 shown in FIG. 12 does not require the use of an anti-slide device (e.g. tapes, clamps, or fasteners) 130 to prevent linear sliding of the plug 650 within the pocket 419 of the receiver 400. For example, the receiver 400 is shown defining opposing grooves 440 aligned generally parallel to the line of insertion 129. The plug 650 includes projections 452 that fit within the grooves to limit lateral movement of the plug 650 relative to the receiver 400.

Figure 13:
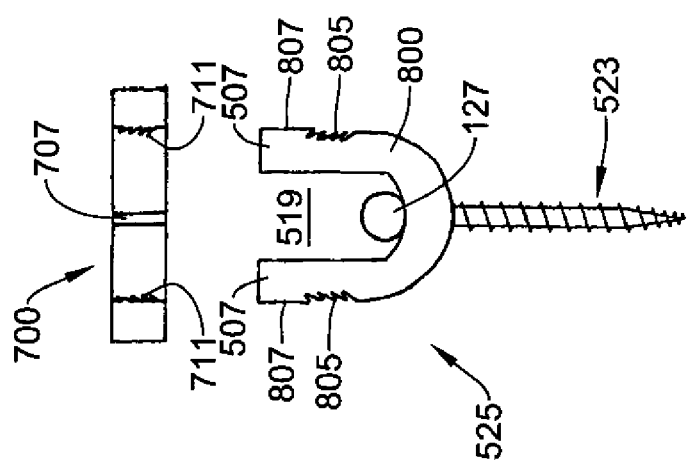
FIG. 13 illustrates still another spinal fixation connector having features that are examples of inventive aspects disclosed herein, the fixation connector includes a locking ring.
Figure 14:
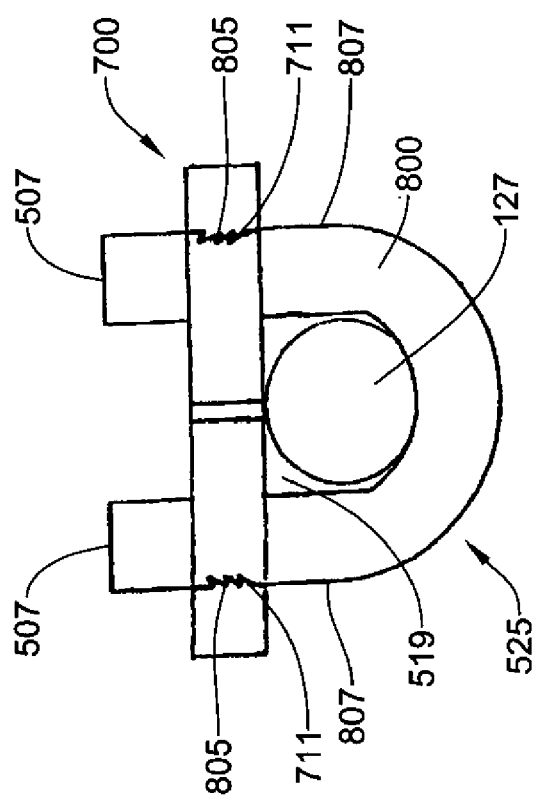
FIG. 14 illustrates the fixation connector of FIG. 13 with a rod secured therein.

FIGS. 13 and 14 illustrate another embodiment of a fixation connector 525 used in stabilization of the vertebrae. The fixation connector 525 includes a bone screw 523 coupled to a receiver 800. The receiver 800 defines an interior pocket 519 for receiving a linking element 127 such as a rod or other member. The embodiment of the fixation connector 525 includes a retaining member 700 adapted to fit around the exterior of the receiver 800 to clamp or otherwise secure the linking element 127 within the pocket 519. The retaining member 700 is adapted to be linearly inserted over the receiver 800 along the insertion line 129. The receiver 800 and the retaining member 700 include intermating teeth 805 and 711 that interlock to fix the retaining member 700 at a desired position relative to the receiver 800. The teeth 805 and 711 preferably hold the retaining member 700 at a position where the linking element 127 is clamped between the retaining member 700 and the receiver 800.

As depicted in FIGS. 13 and 14, the retaining member 700 is depicted as a sleeve. A sleeve such as a complete ring without a split can also be used. The sleeve includes an interior surface 707, which includes interlock structures 711. The sleeve 700 is depicted as a partial ring that can be expanded to facilitate engagement to and disengagement from the receiver 800.

The receiver 800 in FIGS. 13 and 14 is depicted as a U-shape saddle. The saddle includes two legs 507 between which the pocket 519 is defined. The legs 507 include exterior surfaces 807 which include interlocking structures 805.

The teeth 711 and 805 interlock in a manner similar to the teeth of the embodiment of FIGS. 8 and 9, except that the retaining member 700 interlocks with the receiver 800 on the outside of the receiver 800 as compared to being linearly inserted within the receiver. The retaining member 700 flexes outwardly to allow the opposing sets of teeth 711, 805 to progressively snap or ratchet past one another as the retaining member 700 is forced in a downward direction. The sleeve 700 is adapted to elastically deform radially outwardly when inserted over the receiver 800, and then snap inwardly to a position where the corresponding sets of teeth are interlocked.

The ability of the retaining member 700 to elastically deform can be provided by the mechanical properties of the material of the retaining member 700 and/or a combination of structures to enhance deformability (e.g., a slit in the ring making it a partial ring as depicted in FIGS. 13 and 14) and the mechanical properties of the material. The retaining member 700 and/or the receiver 800 can be manufactured from materials of various rigidity such as: Titanium, Nitinol, Stainless Steel, Thermoplastic polymers or Thermoset polymers. Elasticity can also be provided by deflection of the teeth 711, 805, and/or flexing of the legs 807.

Figure 15:
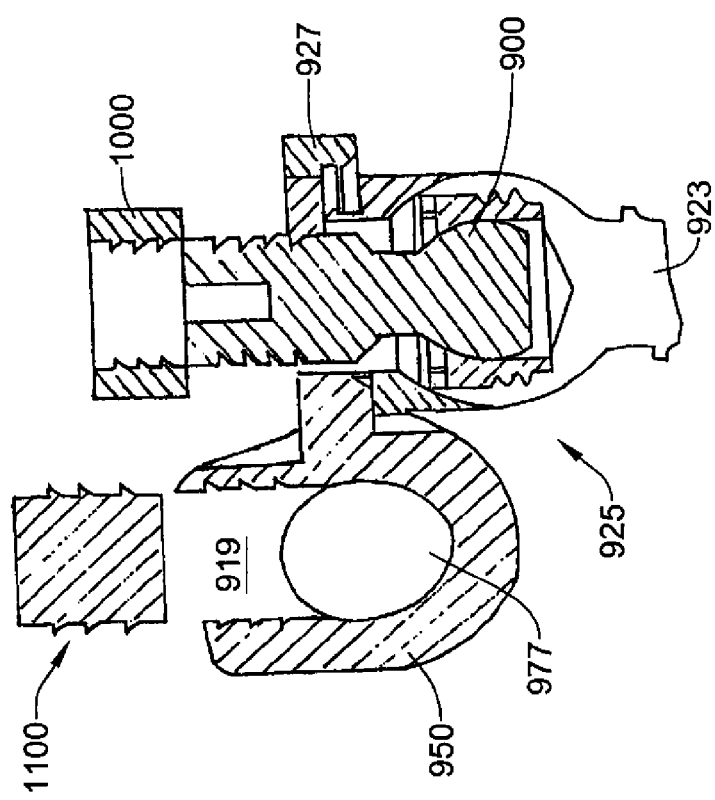
FIG. 15 is a cross sectional view of a further spinal fixation connector having features that are examples of inventive aspects disclosed herein.

FIG. 15 illustrates another embodiment of a fixation connector 925 used in stabilization of the vertebrae. The embodiment shown in FIG. 15 has some features similar to an embodiment disclosed in U.S. Pat. No. 6,050,997, which is incorporated by reference herein in its entirety. The fixation connector 925 shown in FIG. 15 includes a bone engagement structure 923 (e.g., an anchor) adapted for securing the connector 925 to a bone. The connector 925 also includes a first linear interlock component in the form of a shank 900 coupled to the bone engagement structure 923 by a polyaxial connector. The shank 900 is adapted to be coupled to a linking element 927 such as a plate or a rod or another structure. The connector 925 further includes a second linear interlock component in the form of a retaining member 1000 adapted to linearly interlock with the shank 900 to clamp or otherwise secure the linking element 927 to the receiver 900. As shown in FIG. 15, the retaining member 1000 can be in the form of a sleeve such as a ring including interlock structures on the interior surface of the retaining member 1000 adapted to fit around the top end of the shank 900. By linearly interlocking with the interlocking structures of the shank located on the exterior surface of the shank, the retaining member clamps down the linking element 927 in a fixed position.

The linking element 927 is depicted as an offset connector assembly in FIG. 15. The offset assembly linking element 927 further includes a saddle element 950 defining an interior pocket or receptacle 919 for receiving an inter-connector linking element 977 such as a rod or other member adapted to connect two or more connectors 925 that are secured to adjacent vertebral bodies desired to be stabilized. A second retaining member 1100 depicted as a plug is shown in FIG. 15. The retaining member 1100 is inserted into the interior pocket 919 of the saddle element 950 to clamp the inter-connector linking rod 977 with sufficient force to prevent the inter-connector linking rod 977 from sliding relative to the offset connector assembly 927.

The sizes of the interlock structures as well as the spacing between the discrete locking structures in a direction along the line of insertion depicted in all of the figures for all of the embodiments have been exaggerated for diagrammatic purposes. The size and the spacing between each discrete locking structure, e.g., ratchet teeth, will vary depending on a number of factors including the clamping force desired for the application, the materials used, and other factors.

From the foregoing detailed description, it will be evident that modifications and variations can be made in the devices of the invention without departing from the spirit or scope of the invention. Therefore, it is intended that all modifications and variations not departing from the spirit of the invention come within the scope of the claims and their equivalents.

What is claimed is:

1. An orthopedic fixation connection comprising:
a linking element;
a bone anchor;
a saddle including two legs each extending in a first direction from a base portion of the saddle and between which a pocket is defined, the pocket having an open first end opposite the base portion and a second end proximate the base portion adapted to support the linking element within the pocket, the bone anchor coupled to the base portion of the saddle such that the bone anchor extends in a second direction from the base portion of the saddle opposite the first direction;
a first interlock structure positioned within the pocket; and
a plug sized and shaped to be non-rotationally and linearly inserted generally parallel to the first direction into the pocket of the saddle, the plug including a second interlock structure adapted to clamp the linking element between the plug and the second end of the pocket, the second interlock structure non-rotationally interlocking with the first interlock structure when the plug is non-rotationally and linearly inserted into the pocket of the saddle;
wherein the linking element is clamped in the pocket against the second end without the use of a threaded fastener such that the linking element directly contacts the second end of the pocket and the linking element directly contacts a surface of the plug.

2. The orthopedic fixation connector of claim 1, wherein the saddle includes a first plurality of interlock structures and the plug includes a second plurality of interlock structures adapted to interlock with the first plurality of interlock structures when the plug is linearly inserted into the pocket.

3. The orthopedic fixation connector of claim 1, wherein the bone anchor is fixedly coupled to the saddle.

4. The orthopedic fixation connector of claim 1, wherein one of the first and second interlock structures includes at least one discrete locking member, and the other of the first and second interlock structures includes a receptacle for receiving the discrete locking member.

5. The orthopedic fixation connector of claim 1, wherein one of the first and second interlock structures includes at least a first discrete interlocking member, and the other of the first and second interlock structures includes at least a second discrete interlock member that interlocks with the first discrete interlock member when the plug is linearly inserted into the saddle.

6. The orthopedic fixation connector of claim 1, wherein one of the first and second interlock structures includes a plurality of first discrete interlock members, and the other of the first and second interlock structures includes a plurality of second discrete interlock members that interlock with the first discrete interlock members when the plug is linearly inserted into the saddle.

7. The orthopedic fixation connector of claim 1, wherein the first and second interlock structures include teeth that interlock when the plug is linearly inserted into the saddle.

8. The orthopedic fixation connector of claim 7, wherein the teeth are ramped.

9. The orthopedic fixation connector of claim 1, wherein the first interlock structure includes a first plurality of teeth, and the second interlock structure includes a second plurality of teeth.

10. The orthopedic fixation connector of claim 9, wherein the first and second pluralities of teeth comprise ratchet teeth.

11. An orthopedic fixation connector comprising:
a linking element;
a bone anchor;
a receiver including a pair of legs each extending in a first direction from a base portion of the receiver and between which a pocket is defined, the linking element positioned between the pair of legs, the bone anchor coupled to the base portion of the receiver such that the bone anchor extends in a second direction from the base portion of the receiver opposite the first direction; and
a retainer adapted to clamp the linking element between the receiver and the retainer, the retainer non-rotationally interlocking with the receiver when the retainer is non-rotationally and linearly inserted into the pocket generally parallel to the first direction,
wherein the linking element is clamped between the receiver and the retainer without the use of a threaded fastener such that the linking element is in direct contact with a surface of the receiver and in direct contact with a surface of the retainer;
wherein at least one of the receiver and the retainer is elastically deformable between a non-deformed orientation and an elastically deformed orientation different from the non-deformed orientation; and
wherein at least one of the receiver and the retainer moves from the non-deformed orientation to the elastically deformed orientation when the receiver and the retainer are being linearly inserted together, and wherein at least one of the receiver and the retainer self-returns toward the non-deformed orientation to interlock the receiver and the retainer together.

12. The orthopedic fixation connector of claim 11, wherein the retainer and the receiver include interlocking teeth.

13. The orthopedic fixation connector of claim 12, wherein the interlocking teeth are ramped.

14. An orthopedic fixation system comprising:
a bone anchor;
a linking element having a longitudinal axis; and
first and second linear interlocking components adapted to fix the linking element relative to the bone anchor by clamping the linking element between the first and second interlock components such that the linking element is in direct contact with a surface of each of the first and second linear interlocking components, the first and second linear interlock components each having discrete interlock structures that non-rotationally interlock with one another when the second linear interlock component is non-rotationally and linearly inserted into a pocket of the first linear interlock component along a line of insertion generally perpendicular to the longitudinal axis of the linking element;
wherein the bone anchor is coupled to a base portion of the first linear interlocking component opposite an open end of the pocket of the first linear interlocking component;
wherein the linking element is clamped between the first and second linear interlocking components without the use of a threaded fastener.

15. The orthopedic fixation system of claim 14, wherein the discrete interlock structure of the first linear interlocking component includes one or more teeth having a ramp surface oriented at an oblique angle relative to the line of insertion and a locking surface oriented at an oblique angle relative to the line of insertion.

16. The orthopedic fixation system of claim 15, wherein the discrete interlock structure of the second linear interlocking component includes one or more teeth having a ramp surface oriented at an oblique angle relative to the line of insertion and a locking surface oriented at an oblique angle relative to the line of insertion.

17. The orthopedic fixation system of claim 14, wherein the first and second linear interlock components are configured such that the second linear interlock component can be laterally slid from the pocket of the first linear interlocking component in a direction parallel to the longitudinal axis of the linking element.

* * * * *